June 14, 1960 R. S. MOORE Plant Pat. 1,950
MINIATURE ROSE PLANT
Filed Aug. 21, 1959
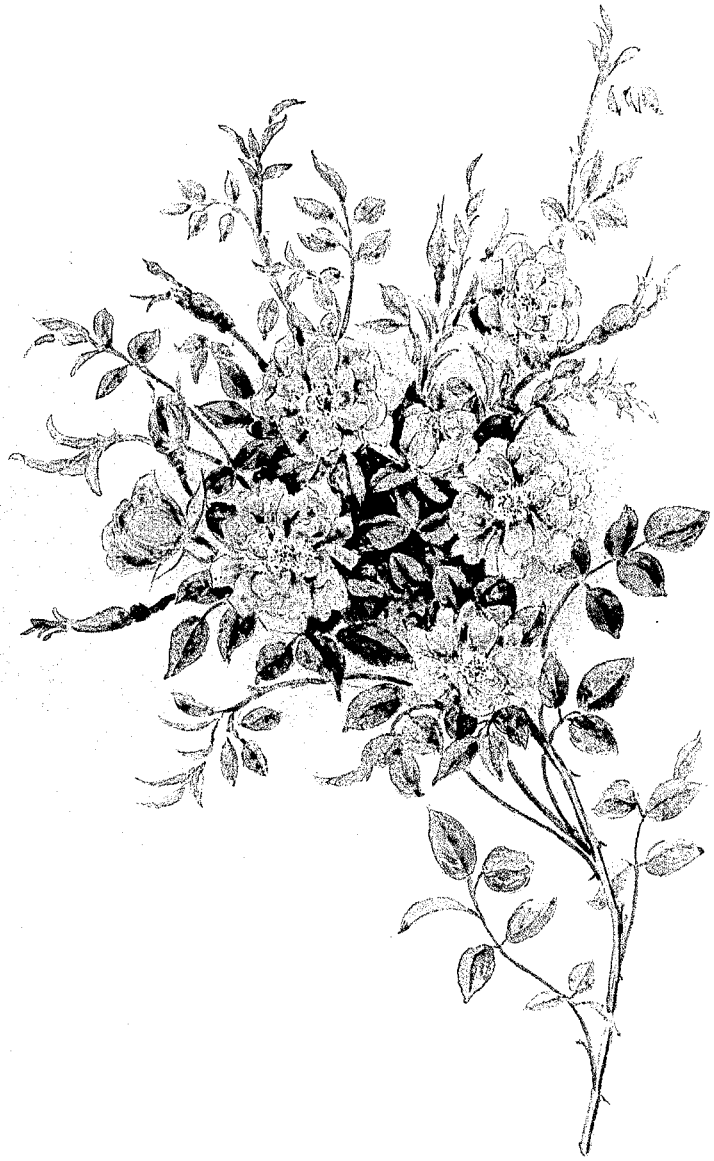
WITNESS
Addison E. Avery
INVENTOR
Ralph S. Moore
Webster & Webster
ATTYS.

United States Patent Office

Plant Pat. 1,950
Patented June 14, 1960

1,950

MINIATURE ROSE PLANT

Ralph S. Moore, 2519 E. Mineral King, Visalia, Calif.

Filed Aug. 21, 1959, Ser. No. 835,380

1 Claim. (Cl. 47—61)

This invention relates to a new and distinct variety of miniature rose plant, of bush type, which is quite compact, roots easily from soft wood cuttings, and bears red flowers having semi-double to double petalage.

The present variety generally resembles the Little Buckaroo rose (United States Plant Patent No. 1,726), but—in comparison—the over-all size of the plant, and its rate of growth, is approximately twenty percent less, and the plant is more compact; the foliage is slightly greener but not as glossy; and the flowers are a lighter shade of red, fade lighter instead of darker, and in general over-all appearance are a brighter red without the white zone which exists in the center of freshly opened flowers of the Little Buckaroo.

The variety was originated by me, in my nursery located as Visalia, California, and under conditions of careful control and observation, as a cross between an unnamed seedling (Rosa Wichuraiana × Floradora) as the seed parent, and an unnamed seedling (Oakington Ruby × Floradora) as the pollen parent; both of the parent varieties being unpatented.

Subsequent to origination of the variety I successfully asexually reproduced it, in my nursery located as aforesaid, by cuttings as well as by budding; such reproductions having run true in all respects.

The figure of the drawing illustrates a spray, including foliage, buds, and flowers.

Referring now specifically to the new and distinct variety of miniature rose plant, the following is a detailed description thereof in outline; all major color plate identifications being—as indicated—either by reference to The British Colour Council Horticultural Colour Chart, or Maerz and Paul Dictionary of Color, except where common terms of color definition are employed.

Type: Dwarf; bush; seedling; greenhouse; outdoor.
Class: Hybrid miniature.

*Flowers*

Continuity: Intermittent to continuous.
Fragrance: Slight; fruit-like.
Flowers borne: Singly, but sometimes several (two—three) to stem; in irregular cluster on strong, medium length stems.
Quantity of bloom: Free, both outdoors and in greenhouse.
Bud:
- *Peduncle.*—Short; medium; erect; stiff. Color—green. Few green-brown hairs.
- *Before calyx breaks.*—Size—small. Form—pointed; oval, with foliaceous appendages on the surface of the bud, and with much cut foliaceous parts extending beyond the tip of the bud equal to one-half its length. Color—green, tinted with bronze.
- *As calyx breaks.*—Color—red.
- *As first petal opens.*—Size—small. Form—pointed; ovoid. Color: outside—chrysanthemum crimson (824/3 British Colour Council); inside—chrysanthemum crimson (824/4 British Colour Council). Opening—opens well.

Bloom:
- *Size when fully open.*—Small, averaging 1¼" to 1½".
- *Petalage.*—Semi-double to double, with from twelve to thirty-five or more petals, depending on season and age of plant.
- *Form.*—Flat; open; loosely rolled outward.

Petals: Thick; satiny both inside and outside.
- *Shape.*—Outside—oval, lanceolate. Intermediate—oval, lanceolate. Inside—lanceolate.
- *Color.*—All petals: outside surface—chrysanthemum crimson (824/3 British Colour Council); inside surface—chrysanthemum crimson (824/2 British Colour Council). The inside surface of the small inner petals often have a white central streak.
- *General color effect.*—Red, brighter and somewhat lighter than the Little Buckaroo rose.
- *Behavior.*—Drop off cleanly.
- *Flower longevity.*—Bush in garden—four to five days or longer. Cut roses grown outdoors, kept at room temperatures—two to four days. Cut flowers grown in greenhouse, kept at room temperatures—two to three days.

Reproductive organs:
- *Stamens.*—Many; arranged irregularly; mixed with petaloids when flower is very double.
- *Filaments.*—Short to medium; most with anthers. Color—white.
- *Anthers.*—Medium size; all open at once. Color—yellow.
- *Pollen.*—Abundant. Color—yellow.
- *Pistils.*—Medium number.
- *Styles.*—Even; short; bunched.
- *Stigma.*—White.
- *Ovaries.*—All enclosed in calyx.
- *Hips.*—None.
- *Sepals.*—Permanent; long; spear shaped; recurved. Color—green.
- *Seeds.*—None.

*Plant*

Foliage:
- *Leaves.*—Compound of five leaflets; abundant; small; leathery; semi-glossy.
- *Leaflets.*—Shape—lanceolate, with apex acute. Base—round. Margin—serrate.
- *Color.*—Mature leaves: upper surface—normal green (23–L–7 Maerz and Paul); under surface—lighter normal green (22–G–6 Maerz and Paul). Young leaves: upper surface—normal green, with bronze tint; under surface—normal green, with bronze tint. On new growth the tips are a reddish brown (7–J–11 to 7–L–9 Maerz and Paul).
- *Rachis.*—Medium. Upper side—smooth, grooved. Under side—sparsely thorny.
- *Stipules.*—Medium length. Medium width, with moderate short points turning out at an angle of about 45 degrees.

Growth:
- *Habit.*—Dwarf; bushy.
- *Growth.*—Free; vigorous.
- *Canes.*—Medium.
- *Main stems.* — Color — green. Thorns — several; hooked downward, with long narrow base. Prickles—none to few. Hairs—none.
- *Branches.*—Color—green (21–L–8 Maerz and Paul). Thorns—several; short; hooked downward, with narrow base; color—light brown (7–E–11 Maerz and Paul). Prickles—none. Hairs—none.
- *New shoots.* — Color — bronze. Thorns — few;

hooked downward. Prickles — none. Hairs — none.

The minature rose plant and its flowers as herein described may vary in slight detail due to climatic and soil conditions under which the variety may be grown; the present description being of the variety as grown at Visalia, California.

The following is claimed:

A new and distinct variety of vigorous, free-growing, miniature rose plant of compact bush type which roots easily from soft wood cuttings and bears red flowers having semi-double to double petalage; the variety generally resembling the Little Buckaroo rose, but—in comparison—the over-all size of the plant, and its rate of growth, is approximately twenty percent less, and the plant is more compact; the foliage is slightly greener but not as glossy; and the flowers are a lighter shade of red, fade lighter instead of darker, and in over-all appearance are a brighter red.

No references cited.